United States Patent
Zhang et al.

(10) Patent No.: US 10,641,774 B2
(45) Date of Patent: May 5, 2020

(54) METHOD FOR DIAGNOSING CANCER BY DETECTING C-TERMINAL SEGMENT OF MOESIN IN BLOOD

(71) Applicant: SHANGHAI KEXIN BIOTECH CO., LTD., Shanghai (CN)

(72) Inventors: Yue Zhang, Shanghai (CN); Jun Bao, Shanghai (CN)

(73) Assignee: SHANGHAI KEXIN BIOTECH CO., LTD., Shanghai (CN)

( * ) Notice: Subject to any disclaimer, the term of this patent is extended or adjusted under 35 U.S.C. 154(b) by 0 days.

(21) Appl. No.: 15/305,657

(22) PCT Filed: Apr. 22, 2015

(86) PCT No.: PCT/CN2015/077162
§ 371 (c)(1),
(2) Date: Oct. 20, 2016

(87) PCT Pub. No.: WO2015/161792
PCT Pub. Date: Oct. 29, 2015

(65) Prior Publication Data
US 2017/0045519 A1 Feb. 16, 2017

(30) Foreign Application Priority Data

Apr. 22, 2014 (WO) ................ PCT/CN2014/075946

(51) Int. Cl.
G01N 33/574 (2006.01)
C12Q 1/6886 (2018.01)

(52) U.S. Cl.
CPC ..... *G01N 33/57496* (2013.01); *C12Q 1/6886* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 2003/0219760 A1* | 11/2003 | Gordon ................ C12Q 1/6886 435/6.18 |
| 2011/0306513 A1 | 12/2011 | Song et al. |
| 2013/0266537 A1* | 10/2013 | Zhang ................ A61K 38/191 424/85.2 |

FOREIGN PATENT DOCUMENTS

| CN | 103298479 A | 9/2013 |
| CN | 103327997 A | 9/2013 |
| CN | 103327998 A | 9/2013 |
| EP | 2278026 A1 | 1/2011 |
| JP | 2014501696 A | 1/2014 |
| WO | WO 2003021229 A2 * | 3/2003 |
| WO | 2006/015079 A2 | 2/2006 |
| WO | 2007/059430 A2 | 5/2007 |
| WO | 2011/009908 A2 | 1/2011 |
| WO | 2012/045274 A1 | 4/2012 |

OTHER PUBLICATIONS

Hong et al. Protein kinase C regulates ezrin-radixin-moesin phosphorylation in canine osteosarcoma. Veterinary and Comparative Oncology 9(3): 207-218, 2010.*
Henry et al. (Molecular Oncology 6: 140-146, 2012).*
Belbin T J et al: "Molecular Profiling of Tumor Progression in Head and Neck Cancer", Archives of Otolaryngology Head and Neck Surg, American Medical Association, US, vol. 131, No. 1, Jan. 1, 2005(Jan. 1, 2005), pp. 10-18, XP009048933.
Venkateshwar G. Keshamouni et al: "Differential Protein Expression Profiling by iTRAQ-2DLC-MS/MS of Lung Cancer Cells Undergoing Epithelial-Mesenchymal Transition Reveals a Migratory/Invasive Phenotype", Journal of Proteome Research., vol. 5, No. 5, May 1, 2006 (May 1, 2006), pp. 1143-1154, XP055409924.
W. Wang: "Identification and Testing of a Gene Expression Signature of Invasive Carcinoma Cells within Primary Mammary Tumors", Cancer Research, vol. 64, No. 23, Dec. 1, 2004 (Dec. 1, 2004), pp. 8585-8594, XP055069643.
Extended European Search Report for EP15782258.6 dated Oct. 4, 2017.

\* cited by examiner

*Primary Examiner* — Alana Harris Dent
(74) *Attorney, Agent, or Firm* — Jun He Law Offices P.C.; James J. Zhu

(57) ABSTRACT

A method for assessing cancer comprising obtaining a biological sample of the subject, detecting a level of a C-terminal segment of moesin in the biological sample, wherein the level of the C-terminal segment of moesin detected in the biological sample of the subject is indicative of the subject developing or with an increased probability of developing cancer. The present application also provides a biomarker and a kit for assessing cancer, and uses of such biomarker. The present application also provides a method of treating cancer.

18 Claims, 3 Drawing Sheets
Specification includes a Sequence Listing.

cDNA Sequence encoding for the Full Length Human Moesin Protein

ATGCCCAAAACGATCAGTGTGCGTGTGACCACCATGGATGCAGAGCTGGAGTTTGCCATCCA
GCCCAACACCACCGGGAAGCAGCTATTTGACCAGGTGGTGAAAACTATTGGCTTGAGGGAAG
TTTGGTTCTTTGGTCTGCAGTACCAGGACACTAAAGGTTTCTCCACCTGGCTGAAACTCAAT
AAGAAGGTGACTGCCCAGGATGTGCGGAAGGAAAGCCCCTGCTCTTTAAGTTCCGTGCCAA
GTTCTACCCTGAGGATGTGTCCGAGGAATTGATTCAGGACATCACTCAGCGCCTGTTCTTTC
TGCAAGTGAAAGAGGGCATTCTCAATGATGATATTTACTGCCCGCCTGAGACCGCTGTGCTG
CTGGCCTCGTATGCTGTCCAGTCTAAGTATGGCGACTTCAATAAGGAAGTGCATAAGTCTGG
CTACCTGGCCGGAGACAAGTTGCTCCCGCAGAGAGTCCTGGAACAGCACAAACTCAACAAGG
ACCAGTGGGAGGAGCGGATCCAGGTGTGGCATGAGGAACACCGTGGCATGCTCAGGGAGGAT
GCTGTCCTGGAATATCTGAAGATTGCTCAAGATCTGGAGATGTATGGTGTGAACTACTTCAG
CATCAAGAACAAGAAAGGCTCAGAGCTGTGGCTGGGGGTGGATGCCCTGGGTCTCAACATCT
ATGAGCAGAATGACAGACTAACTCCCAAGATAGGCTTCCCCTGGAGTGAAATCAGGAACATC
TCTTTCAATGATAAGAAATTTGTCATCAAGCCCATTGACAAAAAGCCCCGGACTTCGTCTT
CTATGCTCCCCGGCTGCGGATTAACAAGCGGATCTTGGCCTTGTGCATGGGGAACCATGAAC
TATACATGCGCCGTCGCAAGCCTGATACCATTGAGGTGCAGCAGATGAAGGCACAGGCCCGG
GAGGAGAAGCACCAGAAGCAGATGGAGCGTGCTATGCTGGAAAATGAAGAAGAAGCGTGA
AATGGCAGAGAAGGAGAAAGAGAAGATTGAACGGGAGAAGGAGGAGCTGATGGAGAGGCTGA
AGCAGATCGAGGAACAGACTAAGAAGGCTCAGCAAGAACTGGAAGAACAGACCCGTAGGGCT
CTGGAACTTGAGCAGGAACGGAAGCGTGCCCAGAGCGAGGCTGAAAAGCTGGCCAAGGAGCG
TCAAGAAGCTGAAGAGGCCAAGGAGGCCTTGCTGCAGGCCTCCCGGGACCAGAAAAAGACTC
AGGAACAGCTGGCCTTGGAAATGGCAGAGCTGACAGCTCGAATCTCCCAGCTGGAGATGGCC
CGACAGAAGAAGGAGAGTGAGGCTGTGGAGTGGCAGCAGAAGGCCCAGATGGTACAGGAAGA
CTTGGAGAAGACCCGTGCTGAGCTGAAGACTGCCATGAGTACACCTCATGTGGCAGAGCCTG
CTGAGAATGAGCAGGATGAGCAGGATGAGAATGGGGCAGAGGCTAGTGCTGACCTACGGGCT
GATGCTATGGCCAAGGACCGCAGTGAGGAGGAACGTACCACTGAGGCAGAGAAGAATGAGCG
TGTGCAGAAGCACCTGAAGGCCCTCACTTCGGAGCTGGCCAATGCCAGAGATGAGTCCAAGA
AGACTGCCAATGACATGATCCATGCTGAGAACATGCGACTGGGCCGAGACAAATACAAGACC
CTGCGCCAGATCCGGCAGGGCAACACCAAGCAGCGCATTGACGAATTTGAGTCTATGTAA
(SEQ ID NO:1)

Figure 1

Amino acid sequence of full length human moesin protein

```
MPKTISVRVT  TMDAELEFAI  QPNTTGKQLF  DQVVKTIGLR  EVWFFGLQYQ
DTKGFSTWLK  LNKKVTAQDV  RKESPLLFKF  RAKFYPEDVS  EELIQDITQR
LFFLQVKEGI  LNDDIYCPPE  TAVLLASYAV  QSKYGDFNKE  VHKSGYLAGD
KLLPQRVLEQ  HKLNKDQWEE  RIQVWHEEHR  GMLREDAVLE  YLKIAQDLEM
YGVNYFSIKN  KKGSELWLGV  DALGLNIYEQ  NDRLTPKIGF  PWSEIRNISF
NDKKFVIKPI  DKKAPDFVFY  APRLRINKRI  LALCMGNHEL  YMRRRKPDTI
EVQQMKAQAR  EEKHQKQMER  AMLENEKKKR  EMAEKEKEKI  EREKEELMER
LKQIEEQTKK  AQQELEEQTR  RALELEQERK  RAQSEAEKLA  KERQEAEEAK
EALLQASRDQ  KKTQEQLALE  MAELTARISQ  LEMARQKKES  EAVEWQQKAQ
MVQEDLEKTR  AELKTAMSTP  HVAEPAENEQ  DEQDENGAEA  SADLRADAMA
KDRSEEERTT  EAEKNERVQK  HLKALTSELA  NARDESKKTA  NDMIHAENMR
LGRDKYKTLR  QIRQGNTKQR  IDEFESM     (SEQ ID NO:2)
```

Figure 2

HVAEPAENEQDEQDENGAEASADLRADAMAKDRSEEERTTEAEKNERVQKHLKAL
TSELANARDESKKTANDMIHAENMRLGRDKYKTLRQIRQGNTKQRIDEFESM (SEQ
ID NO:3)

Figure 3

SEQUENCE LISTING

```
<160> NUMBER OF SEQ ID NOS: 3

<210> SEQ ID NO 1
<211> LENGTH: 1734
<212> TYPE: DNA
<213> ORGANISM: Artificial Sequence
<220> FEATURE:
<223> OTHER INFORMATION: cDNA Sequence encoding for the Full Length
      Human Moesin Protein

<400> SEQUENCE: 1
atgcccaaaa cgatcagtgt gcgtgtgacc accatggatg cagagctgga gtttgccatc       60
cagcccaaca ccaccgggaa gcagctattt gaccaggtgg tgaaaactat tggcttgagg      120
gaagtttggt tctttggtct gcagtaccag gacactaaag gtttctccac ctggctgaaa      180
```

-continued

```
ctcaataaga aggtgactgc ccaggatgtg cggaaggaaa gcccccctgct ctttaagttc      240
cgtgccaagt tctaccctga ggatgtgtcc gaggaattga ttcaggacat cactcagcgc      300
ctgttctttc tgcaagtgaa agagggcatt ctcaatgatg atatttactg cccgcctgag      360
accgctgtgc tgctggcctc gtatgctgtc cagtctaagt atggcgactt caataaggaa      420
gtgcataagt ctggctacct ggccggagac aagttgctcc cgcagagagt cctggaacag      480
cacaaactca caaggacca gtgggaggag cggatccagg tgtggcatga ggaacaccgt       540
ggcatgctca gggaggatgc tgtcctggaa tatctgaaga ttgctcaaga tctggagatg      600
tatggtgtga actacttcag catcaagaac aagaaaggct cagagctgtg gctgggggtg      660
gatgccctgg gtctcaacat ctatgagcag aatgacagac taactcccaa gataggcttc      720
ccctggagtg aaatcaggaa catctctttc aatgataaga aatttgtcat caagcccatt      780
gacaaaaaag ccccggactt cgtcttctat gctccccggc tgcggattaa caagcggatc      840
ttggccttgt gcatgggaa ccatgaacta tacatgcgcc gtcgcaagcc tgataccatt      900
gaggtgcagc agatgaaggc acaggcccgg aggagaagc accagaagca gatggagcgt       960
gctatgctgg aaaatgagaa gaagaagcgt gaaatggcag agaaggagaa agagaagatt      1020
gaacggagagaa aggaggagct gatggagagg ctgaagcaga tcgaggaaca gactaagaag      1080
gctcagcaag aactggaaga acagacccgt agggctctgg aacttgagca ggaacggaag      1140
cgtgcccaga gcgaggctga aaagctggcc aaggagcgtc aagaagctga gaggccaag       1200
gaggccttgc tgcaggcctc ccgggaccag aaaaagactc aggaacagct ggccttggaa      1260
atggcagagc tgacagctcg aatctcccag ctggagatgg cccgacagaa gaggagagt       1320
gaggctgtgg agtggcagca gaaggcccag atggtacagg aagacttgga gaagacccgt      1380
gctgagctga agactgccat gagtacacct catgtggcag agcctgctga gaatgagcag      1440
gatgagcagg atgagaatgg ggcagaggct agtgctgacc tacgggctga tgctatggcc      1500
aaggaccgca gtgaggagga acgtaccact gaggcagaga agaatgagcg tgtgcagaag      1560
caacctgaagg ccctcacttc ggagctggcc aatgccagag atgagtccaa gaagactgcc      1620
aatgacatga tccatgctga aacatgcga ctgggccgag acaaatacaa gaccctgcgc      1680
cagatccggc agggcaacac caagcagcgc attgacgaat ttgagtctat gtaa            1734
```

<210> SEQ ID NO 2
<211> LENGTH: 577
<212> TYPE: PRT
<213> ORGANISM: Artificial Sequence
<220> FEATURE:
<223> OTHER INFORMATION: Amino acid sequence of full length human moesin
      protein

<400> SEQUENCE: 2

Met Pro Lys Thr Ile Ser Val Arg Val Thr Thr Met Asp Ala Glu Leu
1               5                   10                  15

Glu Phe Ala Ile Gln Pro Asn Thr Thr Gly Lys Gln Leu Phe Asp Gln
            20                  25                  30

Val Val Lys Thr Ile Gly Leu Arg Glu Val Trp Phe Phe Gly Leu Gln
        35                  40                  45

Tyr Gln Asp Thr Lys Gly Phe Ser Thr Trp Leu Lys Leu Asn Lys Lys
    50                  55                  60

Val Thr Ala Gln Asp Val Arg Lys Glu Ser Pro Leu Leu Phe Lys Phe
65                  70                  75                  80

Arg Ala Lys Phe Tyr Pro Glu Asp Val Ser Glu Glu Leu Ile Gln Asp

```
                85               90                95
Ile Thr Gln Arg Leu Phe Phe Leu Gln Val Lys Glu Gly Ile Leu Asn
                    100                 105                 110
Asp Asp Ile Tyr Cys Pro Pro Glu Thr Ala Val Leu Leu Ala Ser Tyr
            115                 120                 125
Ala Val Gln Ser Lys Tyr Gly Asp Phe Asn Lys Glu Val His Lys Ser
130                 135                 140
Gly Tyr Leu Ala Gly Asp Lys Leu Leu Pro Gln Arg Val Leu Glu Gln
145                 150                 155                 160
His Lys Leu Asn Lys Asp Gln Trp Glu Glu Arg Ile Gln Val Trp His
                165                 170                 175
Glu Glu His Arg Gly Met Leu Arg Glu Asp Ala Val Leu Glu Tyr Leu
            180                 185                 190
Lys Ile Ala Gln Asp Leu Glu Met Tyr Gly Val Asn Tyr Phe Ser Ile
            195                 200                 205
Lys Asn Lys Lys Gly Ser Glu Leu Trp Leu Gly Val Asp Ala Leu Gly
210                 215                 220
Leu Asn Ile Tyr Glu Gln Asn Asp Arg Leu Thr Pro Lys Ile Gly Phe
225                 230                 235                 240
Pro Trp Ser Glu Ile Arg Asn Ile Ser Phe Asn Asp Lys Lys Phe Val
                245                 250                 255
Ile Lys Pro Ile Asp Lys Lys Ala Pro Asp Phe Val Phe Tyr Ala Pro
            260                 265                 270
Arg Leu Arg Ile Asn Lys Arg Ile Leu Ala Leu Cys Met Gly Asn His
            275                 280                 285
Glu Leu Tyr Met Arg Arg Arg Lys Pro Asp Thr Ile Glu Val Gln Gln
290                 295                 300
Met Lys Ala Gln Ala Arg Glu Glu Lys His Gln Lys Gln Met Glu Arg
305                 310                 315                 320
Ala Met Leu Glu Asn Glu Lys Lys Arg Glu Met Ala Glu Lys Glu
                325                 330                 335
Lys Glu Lys Ile Glu Arg Glu Lys Glu Glu Leu Met Glu Arg Leu Lys
                340                 345                 350
Gln Ile Glu Glu Gln Thr Lys Lys Ala Gln Gln Glu Leu Glu Glu Gln
            355                 360                 365
Thr Arg Arg Ala Leu Glu Leu Glu Gln Glu Arg Lys Arg Ala Gln Ser
            370                 375                 380
Glu Ala Glu Lys Leu Ala Lys Glu Arg Gln Glu Ala Glu Glu Ala Lys
385                 390                 395                 400
Glu Ala Leu Leu Gln Ala Ser Arg Asp Gln Lys Lys Thr Gln Glu Gln
                405                 410                 415
Leu Ala Leu Glu Met Ala Glu Leu Thr Ala Arg Ile Ser Gln Leu Glu
            420                 425                 430
Met Ala Arg Gln Lys Lys Glu Ser Glu Ala Val Glu Trp Gln Gln Lys
            435                 440                 445
Ala Gln Met Val Gln Glu Asp Leu Glu Lys Thr Arg Ala Glu Leu Lys
            450                 455                 460
Thr Ala Met Ser Thr Pro His Val Ala Glu Pro Ala Glu Asn Glu Gln
465                 470                 475                 480
Asp Glu Gln Asp Glu Asn Gly Ala Glu Ala Ser Ala Asp Leu Arg Ala
                485                 490                 495
Asp Ala Met Ala Lys Asp Arg Ser Glu Glu Glu Arg Thr Thr Glu Ala
            500                 505                 510
```

```
Glu Lys Asn Glu Arg Val Gln Lys His Leu Lys Ala Leu Thr Ser Glu
            515                 520                 525

Leu Ala Asn Ala Arg Asp Glu Ser Lys Lys Thr Ala Asn Asp Met Ile
        530                 535                 540

His Ala Glu Asn Met Arg Leu Gly Arg Asp Lys Tyr Lys Thr Leu Arg
545                 550                 555                 560

Gln Ile Arg Gln Gly Asn Thr Lys Gln Arg Ile Asp Glu Phe Glu Ser
                565                 570                 575

Met

<210> SEQ ID NO 3
<211> LENGTH: 107
<212> TYPE: PRT
<213> ORGANISM: Artificial Sequence
<220> FEATURE:
<223> OTHER INFORMATION: Amino acid sequence of 471-577 amino acid
      residues of human moesin protein

<400> SEQUENCE: 3

His Val Ala Glu Pro Ala Glu Asn Glu Gln Asp Glu Gln Asp Glu Asn
1               5                   10                  15

Gly Ala Glu Ala Ser Ala Asp Leu Arg Ala Asp Ala Met Ala Lys Asp
            20                  25                  30

Arg Ser Glu Glu Arg Thr Thr Glu Ala Glu Lys Asn Glu Arg Val
        35                  40                  45

Gln Lys His Leu Lys Ala Leu Thr Ser Glu Leu Ala Asn Ala Arg Asp
    50                  55                  60

Glu Ser Lys Lys Thr Ala Asn Asp Met Ile His Ala Glu Asn Met Arg
65                  70                  75                  80

Leu Gly Arg Asp Lys Tyr Lys Thr Leu Arg Gln Ile Arg Gln Gly Asn
                85                  90                  95

Thr Lys Gln Arg Ile Asp Glu Phe Glu Ser Met
                100                 105
```

METHOD FOR DIAGNOSING CANCER BY DETECTING C-TERMINAL SEGMENT OF MOESIN IN BLOOD

CROSS REFERENCE TO RELATED APPLICATION

This application is a national phase stage filing of international application PCT/CN2015/077162 filed Apr. 22, 2015, which claims priority benefits from international application PCT/CN2014/075946, filed Apr. 22, 2014, the disclosure of which is hereby incorporated by reference in its entirety.

FIELD OF THE INVENTION

The present application generally relates to the field of molecular and cellular biology and detection reagent for cancer.

BACKGROUND OF THE INVENTION

Cancer is a broad group of diseases involving unregulated cell growth. In cancers, cells divide and grow uncontrollably, forming malignant tumors, which may invade nearby parts of the body. Cancer cells may also spread to distant parts of the body through the lymphatic system or bloodstream. There are over 200 different known cancers that affect humans.

Cancer can be detected in a number of ways, including the presence of certain signs and symptoms, screening tests, or medical imaging. Most cancers are initially recognized either because of the appearance of signs or symptoms or through screening. However, these methods usually do not lead to definitive diagnosis, which requires the examination of a tissue sample by a pathologist. The pathological examination is often time-consuming and intrusive. Therefore, there is continuing needs to develop new method for detecting cancer.

The ERM protein family includes ezrin, radixin and moesin. ERM proteins are primarily expressed in cytoplasm, concentrated in actin rich cell-surface structures. They act as structural linkers between the plasma membranes and actin-based cytoskeletons. The ERM proteins share high degrees of inter-species and inter-molecular homologies. The ERM proteins typically have three domains: a N-terminal domain called FERM domain (band four-point-one, ezrin, radixin, moesin homology domain) because of its homology with the band 4.1 protein, a central helical domain and a C-terminal domain. The C-terminal domain binds F-actin while the N-terminal domain is responsible for binding to adhesion molecules in the plasma membrane (Louvet-Vallee (2000)). Several lines of evidence have indicated that $NH_2$- and COOH-terminal domains of ERM proteins are associated intra- and/or intermolecularly in the cytoplasm, which suppresses their binding ability to integral membrane proteins and actin filaments, respectively (Ken Hayashi et al., J. Cell Sci. 112:1149-1158 (1999)).

Moesin is localized in filopodia and other membranous protrusions that are important for cell-cell recognition and signaling and for cell movement (see Louvet-Vallee, Biol. Cell 92:305-16 (2000)). The human moesin protein contains 577 amino acids and typically consists of three domains: the N-terminal FERM domain, the central helical domain and the C-terminal domain. Furthermore, human moesin protein shares high degrees of sequence homology with moesins from other species such as mouse and bovine moesins (Sato et al. Cell Sci. J. 103:131-143(1992)).

BRIEF SUMMARY OF THE INVENTION

The inventors of the present application have surprisingly found that increased level of the C-terminal segment of moesin, but not the full-length moesin protein, is associated with the presence or development of cancer. Therefore, the present application provides a method for assessing the presence or development of cancer, a biomarker and a kit for assessing the presence or development of cancer, and uses of such biomarker and kit. The present application also provides a method for treating cancer.

In one aspect, the present application provides a method for assessing the presence or development of cancer in a subject comprising obtaining a biological sample of the subject, detecting a level of a C-terminal segment of moesin in the biological sample, wherein the level of the C-terminal segment of moesin detected in the biological sample of the subject is indicative of the subject developing or with an increased probability of developing cancer.

In some embodiments, the C-terminal segment used in the method for assessing the presence or development of cancer consists of amino acid residues 471-577 of moesin. In certain embodiments, the moesin is human moesin having an amino acid sequence set forth in SEQ ID NO:2. In some embodiments, the C-terminal segment comprises at least 20 consecutive amino acid residues from the region between amino acid residues 471-577 of human moesin. In some embodiments, the C-terminal segment comprises at least 50 consecutive amino acid residues from the region between amino acid residues 471-577 of human moesin. In some embodiments, the C-terminal segment comprises amino acid residues 471-487, 488-501 or 502-577 of human moesin.

In some embodiments, the level of the C-terminal segment of moesin in the biological sample is detected by contacting the sample with a reagent that specifically binds to the C-terminal segment of moesin. In some preferred embodiments, the reagent is an antibody which specifically binds to the C-terminal segment of moesin or an antibody fragment thereof. In some embodiments, the antibody is a monoclonal antibody.

In some embodiments, the level of the C-terminal segment of moesin detected in the biological sample of the subject is compared to a reference level of the C-terminal segment of moesin detected from reference samples. In some embodiments, higher level of the C-terminal segment of moesin detected in the biological sample than the reference level of the C-terminal segment of moesin is indicative of the subject developing or with an increased probability of developing a cancer. The level of C-terminal segment of moesin detected in the biological sample is at least 2, 3, 4, 5, 6, 7, 8, 9, 10, 15 or 20 times the reference level of the C-terminal segment of moesin. In some embodiments, the level of C-terminal segment of moesin detected in the biological sample is preferably at least 2 times the reference level of the C-terminal segment of moesin. In some embodiments, the level of C-terminal segment of moesin detected in the biological sample is at least 5 times the reference level of the C-terminal segment of moesin. In some embodiments, the reference sample is from a non-tumoral subject, which is a subject that has no clinically detectable tumor.

In some embodiments, the biological sample is selected from the group consisting of whole blood, serum and plasma. In some embodiments, the biological sample is urine or saliva.

In some embodiments, the cancer is selected from the group consisting of acute lymphoblastic leukemia, acute myeloid leukemia, adrenocortical carcinoma, anal cancer, appendix cancer, astrocytoma, basal-cell carcinoma, bile duct cancer, bladder cancer, otseosarcoma, brainstem glioma, brain cancer, cerebellar astrocytoma, ependymoma, medulloblastoma, breast cancer, bronchial adenoma, Burkitt's lymphoma, carcinoid tumor, gastrointestinal carcinoid tumor, cervical cancer, chronic bronchitis, chronic lymphocytic leukemia, chronic myelogenous leukemia, chronic myeloproliferative disorders, chronic obstructive pulmonary disease, colon cancer, cutaneous T-cell lymphoma, emphysema, endometrial cancer, enpendymoma, Ewing's sarcoma, extracranial germ cell tumor, extragonadal germ cell tumor, extrahepatic bile duct cancer, retinoblastoma, gallbladder cancer, gastric cancer, glioma, hairy cell leukemia, head and neck cancer, heart cancer, liver cancer, Hodgkin lymphoma, hypopharyngeal cancer, intraocular melanoma, islet cell carcinoma, Kaposi sarcoma, kidney cancer, laryngeal cancer, leukemia, lung cancer, melanoma, neuroblastoma, non-Hodgkin lymphoma, ovarian cancer, pancreatic cancer, parathyroid cancer, penile cancer, plasma cell neoplasia, pleuropulmonary blastoma, prostate cancer, rectal cancer, renal cell carcinoma, retinoblastoma, soft tissue sarcoma, uterine sarcoma, skin cancer, squamous cell carcinoma, stomach cancer, throat cancer, thyroid cancer, uterine cancer, vaginal cancer, vulvar cancer.

In another aspect, the present application provides a biomarker for assessing the presence or development of cancer consisting essentially of the C-terminal segment of moesin. In some embodiments, the C-terminal segment of moesin consists of amino acid residues 471-577 of human moesin. In some embodiments, the biomarker comprises at least 20 consecutive amino acid residues of the amino acid residues 471-577 of human moesin. In some embodiments, the biomarker comprises at least 50 consecutive amino acid residues of the amino acid residues 471-577 of human moesin. In some embodiments, the biomarker comprises at least 10, 15, 20, 25, 30, 35, 40, 45, 50, 55, 60, 65, 70, 75, 80, 85, 90, 95 or 100 consecutive amino acid residues of the amino acid residues 471-577 of human moesin. The present application also provides the use of the C-terminal segment of moesin as a biomarker for assessing the presence or development of cancer in a subject, and for the manufacture of a detection agent for assessing cancer in a subject. In some embodiments, the C-terminal segment comprises amino acid residues 471-487, 488-501 or 502-577 of human moesin. In some embodiments, the human moesin has an amino acid sequence as set forth in SEQ ID NO:2.

In another aspect, the present application provides a kit for assessing the presence or development of cancer in a subject comprising a reagent that specifically binds to the C-terminal segment of moesin. In some embodiments, the reagent is an antibody. In some embodiments, the reagent is a monoclonal antibody or a fragment thereof.

In another aspect, the present application provides a method of treating cancer in a subject comprising administering to the subject a pharmaceutical composition comprising a reagent that specifically modulates the function of the C-terminal segment of moesin and a pharmaceutically acceptable excipient. In some embodiments, the reagent specifically binds to the C-terminal segment of moesin. In some embodiments, the reagent is an antibody. In some embodiments, the reagent is a monoclonal antibody or a fragment thereof. In another aspect, the present application provides the use of the C-terminal segment of moesin for the manufacture of a medicament for treating cancer in a subject.

BRIEF DESCRIPTION OF THE FIGURES

FIG. 1. cDNA sequence encoding for the full length human moesin protein (SEQ ID NO: 1).

FIG. 2. Amino acid sequence of full length human moesin protein (SEQ ID NO:2).

FIG. 3. Amino acid sequence of 471-577 amino acid residues of human moesin protein (SEQ ID No: 3).

DETAILED DESCRIPTION OF THE INVENTION

Figure 4:
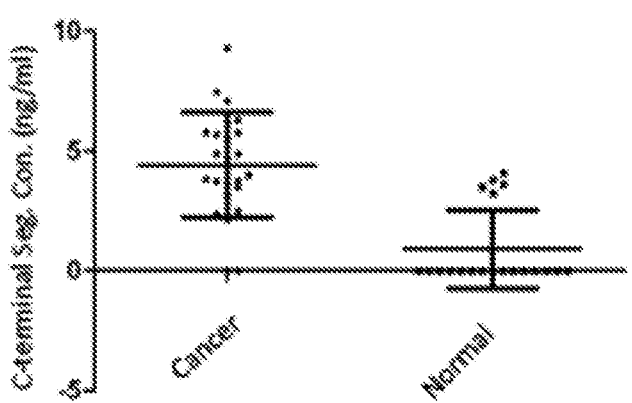
FIG. 4. Concentration of C-terminal moesin segment in samples of cancer patients and healthy individuals (normal).

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, solid state chemistry, inorganic chemistry, organic chemistry, physical chemistry, analytical chemistry, materials chemistry, biochemistry, biology, molecular biology, recombinant DNA techniques, pharmacology, imaging, and the like, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" series (Academic Press, Inc.); "Current Protocols in Molecular Biology" (F. M. Ausubel et al., eds., 1987, and periodic updates); "PCR: The Polymerase Chain Reaction", (Mullis et al., eds., 1994). Primers, polynucleotides and polypeptides employed in the present application can be generated using standard techniques known in the art.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

The following embodiments are put forth so as to provide those of ordinary skill in the art with a complete disclosure and description of how to perform the methods and use the biomarkers and kits disclosed and claimed herein. Efforts have been made to ensure accuracy with respect to numbers (e.g., amounts, temperature, etc.), but some errors and deviations should be accounted for.

It must be noted that, as used in the specification and the appended claims, the singular forms "a," "an," and "the" include plural forms of the same unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

The present application provides a method for assessing the presence or development of cancer, a biomarker and a kit for assessing the presence or development of cancer, and uses of such biomarker and kit. The present application also provides a method for treating cancer.

Method for Assessing the Presence or Development of Cancer

The first aspect of the present application provides a method for assessing the presence or development of cancer in a subject. The method comprises obtaining a biological sample of the subject and detecting a level of a C-terminal segment of moesin in the biological sample. The level of the C-terminal segment of moesin detected in the biological sample of the subject is indicative of the subject developing or with an increased probability of developing cancer.

The term "assess" or "assessment" as used herein, relates to the capacity of discriminating between samples from subjects affected and not affected by cancer or the capacity of discriminating between samples from subjects that have different stages of cancer development before entering into metastasis. In certain embodiments, the assessment relates to the determination of whether a subject has tumor or not. In certain embodiments, the assessment relates to the determination of whether a subject's tumor has lessened or become more severe. In certain embodiments, the assessment can help evaluate the likelihood of clinical benefit from a therapy. In certain embodiments, the assessment may relate to whether and/or the probability that a patient will improve following treatment, for example, treatment with a particular therapeutic agent. The assessing methods of the present application can be used clinically to make treatment decisions by choosing the most appropriate treatment modalities for any particular patient. The assessing methods of the present application can be valuable tools in evaluating whether long-term survival of the patient, following a therapeutic regimen, such as a given therapeutic regimen, including for example, administration of a given therapeutic agent or combination, surgical intervention, steroid treatment, etc., is likely.

The discriminating or discrimination as understood by a person skilled in the art cannot aim to be correct in 100% of the samples analyzed. However, it requires that a statistically significant quantity of the samples analyzed is correctly classified. The quantity that is statistically significant can be established by a person skilled in the art by the use of different statistical tools, for example, but without being limited to, by the determination of confidence intervals, determination of p value, Student test or Fisher's discriminating functions. Details are found in Dowdy and Wearden, Statistics for Research, John Wiley & Sons, New York 1983. In certain embodiments, the confidence intervals are at least 90%, at least 95%, at least 97%, at least 98% or at least 99%. In certain embodiments, the p value is less than 0.1, 0.05, 0.01, 0.005 or 0.0001. In certain embodiments, the present application makes it possible to correctly detect cancer in at least 50%, at least 55%, at least 60%, at least 65%, at least 70%, at least 75%, at least 80%, at least 85%, at least 90%, or at least 95% of the subjects of certain group of population analyzed.

A "biological sample" as used herein refers to a biological composition that is obtained or derived from a subject of interest that contains a cellular and/or other molecular entity that is to be characterized and/or identified, for example based on physical, biochemical, chemical and/or physiological characteristics. A biological sample includes, but is not limited to, cells, tissues, organs and/or biological fluids of a subject, obtained by any method known by a person skilled in the art. In certain embodiments, the biological sample is a fluid sample. In certain embodiments, the fluid sample is whole blood, plasma or blood serum. Preferably, the fluid sample is blood serum.

The term "subject" as used herein refers to animals, preferably mammals, and more preferably, humans. The term "subject" does not aim to be limiting in any aspect, and can be of any age, sex and physical condition.

The term "moesin" stands for membrane-organizing extension spike protein, as described in Lankes and Furthmayr (1991) Proc. Natl. Acad. Sci., 88:8297-8301. The amino acid sequence of the moesin polypeptide can be found in public database, such as the National Center for Biotechnology Information. The terms polypeptide and protein are used interchangeable throughout this application. In certain embodiments, the moesin is a human moesin. Full length human moesin protein is a 577-amino acid polypeptide having an amino acid sequence as set forth in SEQ ID NO:2. Human moesin protein shares high degrees of sequence homology with moesins from other species such as mouse and bovine moesins (Sato et al. *Cell Sci. J* 103:131-143 (1992)).

The "C-terminal segment of moesin" refers to the C-terminal tail domain of the moesin protein or a portion of the C-terminal tail domain. The C-terminal tail domain of moesin refers to the portion of the wild type moesin protein structurally proximate to the carboxy-terminal of the protein and functionally responsible for binding to and interacting with actin filaments. The C-terminal tail domain of moesin is positively charged and adopts an extended, meandering structure. Specifically, the term refers to the last about 107 amino acid residues of human moesin protein. In certain literatures, the same domain is also known as C-ERM associated domain (C-ERMAD), which is included in the definition herein (Bretscher et al. (1995)). The last 34 amino acid residues of the C-terminal domain are highly conserved amongst ERM proteins and form the region for binding to F-actin. In particular, the term "C-terminal segment of moesin" contains polypeptides having at least 10, 15, 20, 25, 30, 35, 40, 45, 50, 55, 60, 65, 70, 75, 80, 85, 90, 95 or 100 consecutive amino acid residues of the amino acid sequences within the last about 107 amino acid residues of human moesin protein. In certain embodiments, the C-terminal segment of moesin consists of the amino acid residues 471-577 of huma moesin as set forth in SEQ ID NO: 3. Preferably, the C-terminal segment of moesin comprises at least 20 consecutive amino acid residues from the region between amino acid residues 471-577 of human moesin. More preferably, the C-terminal segment comprises at least 50 consecutive amino acid residues from the region between amino acid residues 471-577 of human moesin.

The term "level of C-terminal segment of moesin" as used herein refers to the amount or concentration of the C-terminal segment of moesin detected in a sample. The term "detection" as used herein refers to any method of measuring the amount or concentration of the C-terminal segment of moesin. The detection method can be semi-quantitative or quantitative. Measuring can be done directly or indirectly. Direct measuring relates to measuring the amount or concentration of the peptide based on a signal which is obtained from the peptide itself and the intensity of which directly correlates with the number of molecules of the peptide present in the sample. Such a signal—sometimes referred to herein as intensity signal—may be obtained, e.g., by measuring an intensity value of a specific physical or chemical property of the peptide. Indirect measuring includes measuring of a signal obtained from a secondary component (i.e. a component not being the peptide or polypeptide itself) or a biological read out system, e.g., measurable cellular responses, ligands, labels, or enzymatic reaction products.

In accordance with the present application, detecting the level of the C-terminal segment of moesin can be achieved by any suitable means for determining the amount of a peptide in a sample. In certain embodiments, the detection methods include immunoassay devices and methods which may utilize labeled molecules in various sandwich, competition, or other assay formats. Said assays will develop a signal which is indicative of the presence or absence of the peptide of interest. Moreover, the signal strength can, preferably, be correlated directly or indirectly (e.g., reverse-proportional) to the amount of the peptide of interest present in a sample. Further suitable methods include measuring a physical or chemical property specific for the peptide of interest such as its precise molecular mass or NMR spectrum. Suitable detection methods may also include biosensors, optical devices coupled to immunoassays, biochips, analytical devices such as mass-spectrometers, NMR-analyzers, or chromatography devices. Further, suitable detection methods may include micro-plate ELISA-based methods, fully-automated or robotic immunoassays (available for example on ELECSYS analyzers), CBA (an enzymatic Cobalt Binding Assay, available for example on Roche-Hitachi analyzers), and latex agglutination assays (available for example on Roche-Hitachi analyzers). In certain embodiments, the level of a peptide of interest is detected by measuring a specific intensity signal obtainable from the peptide in the sample. As described above, such a signal may be the signal intensity observed at an m/z (mass to charge ratio) variable specific for the peptide of interest observed in mass spectra or a NMR spectrum specific for the peptide of interest.

In certain embodiments, the level of the C-terminal segment of moesin is detected by contacting the sample with a reagent that specifically binds to the C-terminal segment of moesin. The bound reagent will generate an intensity signal. Binding according to the present application includes both covalent and non-covalent binding. A reagent binding to the C-terminal segment of moesin according to the present application can be any compound, e.g., a peptide, polypeptide, nucleic acid, or small molecule, binding to the C-terminal segment of moesin described herein. In certain embodiments, the binding reagents include antibodies, nucleic acids, peptides or polypeptides such as receptors or binding partners for the peptide or fragments thereof containing the binding domains for the peptides, and aptamers, e.g., nucleic acid or peptide aptamers. Methods to prepare such reagents are well-known in the art. For example, identification and production of suitable antibodies or aptamers is also offered by commercial suppliers. The person skilled in the art is familiar with methods to develop derivatives of such reagents with higher affinity or specificity. For example, random mutations can be introduced into the nucleic acids, peptides or polypeptides. These derivatives can then be tested for binding according to screening procedures known in the art, e.g., phage display.

Specific binding according to the present application means that the reagent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g., according to its size on a Western Blot, or by its relatively higher abundance in the sample. Binding of the reagent can be measured by any method known in the art. Preferably, said method is semi-quantitative or quantitative. Suitable methods include: (1) binding of a reagent may be measured directly, e.g., by NMR or surface plasmon resonance; (2) If the reagent also serves as a substrate of an enzymatic activity of the peptide of interest, an enzymatic reaction product may be measured (e.g., the amount of a protease can be measured by measuring the amount of cleaved substrate, e.g., on a Western Blot). Alternatively, the reagent may exhibit enzymatic properties itself and the reagent which was bound by the peptide, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g., detectable) amount of product can be measured. (3) The reagent may be coupled covalently or non-covalently to a label allowing detection and measurement of the reagent. Labeling may be done by direct or indirect methods. Direct labeling involves coupling of the label directly (covalently or non-covalently) to the reagent. Indirect labeling involves binding (covalently or non-covalently) of a secondary reagent to the first reagent. The secondary reagent should specifically bind to the first reagent. Said secondary reagent may be coupled with a suitable label and/or be the target (receptor) of tertiary reagent binding to the secondary reagent. The use of secondary, tertiary or even higher order reagents is often to increase the signal intensity. Suitable secondary and higher order reagents may include antibodies, secondary antibodies, and the well-known streptavidin-biotin system (Vector Laboratories, Inc.). The reagent or substrate may also be "tagged" with one or more tags as known in the art. Such tags may then be targets for higher order reagents. Suitable tags include biotin, digoxygenin, His-Tag, Glutathion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus.

Suitable labels are any labels detectable by an appropriate detection method. Typical labels include gold particles, latex beads, acridan ester, luminol, ruthenium, enzymatically active labels, radioactive labels, magnetic labels ("e.g., magnetic beads", including paramagnetic and superparamagnetic labels), and fluorescent labels. Enzymatically active labels include e.g., horseradish peroxidase, alkaline phosphatase, beta-Galactosidase, Luciferase, and derivatives thereof. Suitable substrates for detection include di-amino-benzidine (DAB), 3,3'-5,5'-tetramethylbenzidine, NBT-BCIP (4-nitro blue tetrazolium chloride and 5-bromo-4-chloro-3-indolyl-phosphate, available as ready-made stock solution from Roche Diagnostics), CDP-Star (Amersham Biosciences), ECF (Amersham Biosciences). A suitable enzyme-substrate combination may result in a colored reaction product, fluorescence or chemiluminescence, which can be measured according to methods known in the art (e.g., using a light-sensitive film or a suitable camera system). As for measuring the enzymatic reaction, the criteria given above apply analogously.

Typical fluorescent labels include fluorescent proteins (such as GFP and its derivatives), Cy3, Cy5, Texas Red, Fluorescein, and the Alexa dyes (e.g., Alexa 568). Further fluorescent labels are available e.g., from Molecular Probes (Oregon). Also the use of quantum dots as fluorescent labels is contemplated. Typical radioactive labels include 35S, 125I, 32P, 33P and the like. A radioactive label can be detected by any method known and appropriate, e.g., a light-sensitive film or a phosphor imager. Suitable measurement methods according the present application also include precipitation (particularly immunoprecipitation), electro-chemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoro immuno assay (DELFIA), scintillation, proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), Western Blotting, and mass spectrometry), can be used alone or in combination with labeling or other detection methods as described above.

In certain preferred embodiments, the reagent that specifically binds to the C-terminal segment of moesin is an antibody or an antibody fragment. An antibody as referred to herein includes both polyclonal and monoclonal antibodies, multivalent antibodies, multispecific antibodies (e.g., bispecific antibodies), as well as fragments thereof, such as single chain antibodies, Fv, Fab and F(ab)2 fragments that are capable of binding antigen or hapten.

In certain embodiments, the antibody is preferably a monoclonal antibody. Monoclonal antibodies are highly specific, being directed against a single antigen. In certain embodiments, a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In order to screen for antibodies which bind to an epitope on an antigen bound by an antibody of interest, a routine cross-blocking assay such as that described in *Antibodies, A Laboratory Manual*, Cold Spring Harbor Laboratory, Ed Harlow and David Lane (1988), can be performed.

In certain embodiments, the level of C-terminal segment of moesin may be detected as follows: (a) contacting a solid support comprising a reagent that specifically binds to the C-terminal segment of moesin as specified above with a sample comprising the C-terminal segment of moesin and (b) measuring the amount of C-terminal segment of moesin which is bound to the support. The reagent, preferably chosen from the group consisting of nucleic acids, peptides, polypeptides, antibodies and aptamers, is preferably present on a solid carriers in immobilized form. The reagent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said reagent to carriers are well known and include, but are not limited to ionic, hydrophobic, covalent interactions and the like. It is also contemplated to use "suspension arrays" as arrays according to the present application (Nolan 2002, Trends Biotechnol. 20(1):9-12). In such suspension arrays, the carrier, e.g., a microbead or microsphere, is present in suspension. The array consists of different microbeads or microspheres, possibly labeled, carrying different reagents. Methods of producing such arrays, for example based on solid-phase chemistry and photo-labile protective groups, are generally known (U.S. Pat. No. 5,744,305).

In certain embodiments, the level of C-terminal segment of moesin is detected in a blood sample obtained from a subject as defined in the present application. Preferably, such a determination is done by ELISA.

In certain embodiments, the level of the C-terminal segment of moesin detected in the biological sample of the subject is compared to a reference level of the C-terminal segment of moesin detected from reference samples.

The term "compare" as used herein encompasses comparing the level of the C-terminal segment of moesin comprised by the biological sample to be analyzed with a level of a suitable reference sample. It is to be understood that the term as used herein refers to a comparison of corresponding parameters or values, e.g., an absolute amount is compared to an absolute reference amount while a concentration is compared to a reference concentration or an intensity signal obtained from a test sample is compared to the same type of intensity signal of a reference sample. The comparison may be carried out manually or computer assisted. For a computer assisted comparison, the value of the determined amount may be compared to values corresponding to suitable references which are stored in a database by a computer program. The computer program may further evaluate the result of the comparison, and automatically provide the desired assessment in a suitable output format. Based on the comparison of the level of the C-terminal segment of moesin detected to suitable reference level(s), it is possible to assess cancer in said subject.

Accordingly, the term "reference level" as used herein refers to a threshold level which allows for ruling in or ruling out the presence or development of cancer in a subject. For example, if the level of C-terminal segment of moesin of a sample is higher than the reference level, then the sample may be considered as developing or with an increased probability of developing cancer. A reference level of the C-terminal segment of moesin may be derived from one or more reference samples wherein the reference level is obtained from experiments conducted in parallel with the experiment for testing the sample of interest. Alternatively, a reference level may be obtained in a database, which includes a collection of data, standard, or level from one or more reference samples or disease reference samples. In certain embodiments, such collection of data, standard or level are normalized so that they can be used for comparison purpose with data from one or more samples. "Normalize" or "normalization" is a process by which a measurement raw data is converted into data that may be directly compared with other so normalized data. Normalization is used to overcome assay-specific errors caused by factors that may vary from one assay to another, for example, variation in loaded quantities, binding efficiency, detection sensitivity, and other various errors. In certain embodiment, a reference database includes concentrations of the C-terminal segment of moesin and/or other laboratory and clinical data from one or more reference samples. In certain embodiments, a reference database includes levels of the C-terminal segment of moesin that are each normalized as a percent of the level of the C-terminal segment of moesin of a control sample (e.g. a known amount of the C-terminal segment of moesin) tested under the same conditions as the reference samples. In order to compare with such normalized levels of the C-terminal segment of moesin, the level of the C-terminal segment of moesin of a test sample is also measured and calculated as a percent of the level of the C-terminal segment of moesin of the control sample tested under the same conditions as the test sample. In certain embodiments, a reference database is established by compiling reference level data from reference samples obtained from healthy subjects and/or non-tumoral subjects (i.e., subjects that are known not to have cancer). In certain embodiments, a reference database is established by compiling reference level data from reference samples from individuals under treatment for cancer. In certain embodiments, a reference database is established by compiling data from reference samples from individuals at different stages of cancer as evidenced by, for example, different levels of the C-terminal segment of moesin.

A reference level may be chosen by the persons skilled in the art according to the desired sensitivity and specificity. Means for determining suitable reference levels are known to the persons skilled in the art, e.g., a reference level can be determined from Receiver-Operator-Curves (ROC) according to clinical studies.

In some embodiments, higher level of the C-terminal segment of moesin detected in the biological sample than the reference level of the C-terminal segment of moesin is indicative of the subject developing or with an increased probability of developing a cancer. Preferably, the level of C-terminal segment of moesin detected in the biological sample is at least 2 times the reference level of the C-terminal segment of moesin. More preferably, the level of C-terminal segment of moesin detected in the biological sample is at least 5 times the reference level of the C-terminal segment of moesin.

An "increased probability" as used herein the present application refers to an overall increase of 5%, 10%, 15%, 20%, 25%, 30%, 40%, 50%, 60%, 70%, 80%, 85%, 90%, 95%, 96%, 97%, 98%, 99% or greater, in the level of likelihood that a subject will develop cancer, as compared to a subject from which a reference sample is obtained.

The term "cancer" used herein refers to a broad group of diseases involving unregulated cell growth. Examples of cancers include without limitation, acute lymphoblastic leukemia, acute myeloid leukemia, adrenocortical carcinoma, anal cancer, appendix cancer, astrocytoma, basal-cell carcinoma, bile duct cancer, bladder cancer, otseosarcoma, brainstem glioma, brain cancer, cerebellar astrocytoma, ependymoma, medulloblastoma, breast cancer, bronchial adenoma, Burkitt's lymphoma, carcinoid tumor, gastrointestinal carcinoid tumor, cervical cancer, chronic bronchitis, chronic lymphocytic leukemia, chronic myelogenous leukemia, chronic myeloproliferative disorders, chronic obstructive pulmonary disease, colon cancer, cutaneous T-cell lymphoma, emphysema, endometrial cancer, enpendymoma, Ewing's sarcoma, extracranial germ cell tumor, extragonadal germ cell tumor, extrahepatic bile duct cancer, retinoblastoma, gallbladder cancer, gastric cancer, glioma, hairy cell leukemia, head and neck cancer, heart cancer, liver cancer, Hodgkin lymphoma, hypopharyngeal cancer, intraocular melanoma, islet cell carcinoma, Kaposi sarcoma, kidney cancer, laryngeal cancer, leukemia, lung cancer, melanoma, neuroblastoma, non-Hodgkin lymphoma, ovarian cancer, pancreatic cancer, parathyroid cancer, penile cancer, plasma cell neoplasia, pleuropulmonary blastoma, prostate cancer, rectal cancer, renal cell carcinoma, retinoblastoma, soft tissue sarcoma, uterine sarcoma, skin cancer, squamous cell carcinoma, stomach cancer, throat cancer, thyroid cancer, uterine cancer, vaginal cancer, vulvar cancer.

Biomarker and Kit

Another aspect of the present application provides a biomarker for assessing cancer consisting essentially of the C-terminal segment of moesin or a portion of the C-terminal segment.

As used herein, a "biomarker" refers to a target molecule that indicates or is a sign of a normal or abnormal process in a subject or of a disease or other condition in a subject.

Biomarkers are usually detectable and measurable by a variety of methods including laboratory assays and medical imaging.

In certain embodiments, the biomarker of the present application comprises at least 20 consecutive amino acid residues of the C-terminal segment of moesin. In certain embodiments, the biomarker of the present application comprises at least 50 consecutive amino acid residues of the C-terminal segment of moesin. In certain embodiments, the C-terminal segment of moesin consists of amino acid residues 471-577 of human moesin.

In another aspect, the present application provides use of the C-terminal segment of moesin as a biomarker for assessing the presence or development of cancer in a subject.

In another aspect, the present application relates to use of the C-terminal segment of moesin for the manufacture of a detection agent for assessing the presence or development of cancer in a subject.

In another aspect, the present application provides a kit for assessing cancer in a subject, wherein the kit contains means for detecting the level of the C-terminal segment of moesin present in a sample. The kit may use any means suitable for detecting the level of the C-terminal segment of moesin present in a sample. In certain embodiments, the kit contains a reagent that specifically binds to the C-terminal segment of moesin. The term "reagent" and "specifically binds" have been disclosed above in the present application. In a preferred embodiment, the reagent is an antibody.

In certain embodiments, the kit may additionally contain a user's manual for interpreting the results of any measurement(s) with respect to assessing cancer in a subject as defined in the present application. Particularly, such manual may include information about what determined levels corresponds to what kind of assessment. Additionally, such user's manual may provide instructions about correctly using the components of the kit for detecting the level of the C-terminal segment of moesin. In certain embodiments, the means for detection and the instruction manual of the kit are provided within a single container.

Method of Treating Cancer

Another aspect of the present application relates to a method of treating cancer in a subject. The method comprises administering to the subject a pharmaceutical composition comprising a reagent that specifically modulates the function of the C-terminal segment of moesin and a pharmaceutically acceptable excipient.

The term "treat" as used herein refers to clinical intervention in an attempt to alter the natural course of a disease or condition in a subject being treated, and can be performed either for prophylaxis or during the course of clinical pathology. Desirable effect of treatment include preventing occurrence or recurrence of the disease or condition, alleviation of symptoms, diminishment of any direct or indirect pathological consequences of the disease or condition, decreasing the rate of progression of the disease or condition, amelioration or palliation of the disease state, and remission or improved prognosis.

The term "modulate", as used herein, refers to control, as well as regulate the function of the C-terminal segment of moesin. For example, the reagent may specifically bind to the C-terminal segment of moesin and sequester the C-terminal segment from interacting with other molecules. For another example, the reagent may compete with the C-terminal segment for binding with its interacting partner such as an adhesion molecule that the C-terminal tail domain of moesin usually binds to. For another example, the reagent may modify the C-terminal segment (e.g., phosphorylation) such that the property of the C-terminal segment is altered. For yet anther example, the reagent may degrade the C-terminal segment of moesin and remove it from the subject.

In certain embodiments, the reagent specifically binds to the C-terminal segment of moesin. In a preferred embodiment, the reagent is an antibody. More preferably, the reagent is a monoclonal antibody or a fragment thereof. In certain embodiments, the reagent is a humanized hybrid antibody wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art.

In certain embodiments, the reagent can compete with the C-terminal segment of moesin for binding to an adhesion molecule or plasma membrane or other cellular or molecular component that the C-terminal domain of moesin normally binds to. In a preferred embodiment, the reagent is an isolated peptide consisting essentially of the C-terminal segment of moesin or a variant thereof.

The term "isolated" as used herein, refers to peptides or nucleotides which: 1) are substantially free from components that normally accompany or interact with it in nature, or 2) if it is found in its natural medium, they have been altered by human intervention and/or introduced in a cell which does not originally possess it.

The term "variant" as used herein, refers to a peptide (or a nucleotide) substantially homologous to a peptide (or nucleotide) of interest that has an identical physiological, metabolic or immunological effect, or have the same use as the peptide (or nucleotide) of interest. A peptide variant also includes the peptides resulting from post-translational modifications such as, but without being limited to, glycosylation, phosphorylation or methylation of the peptide of interest.

As used here, a peptide (or nucleotide) variant is "substantially homologous" to a peptide (or nucleotide) of interest when the sequence of amino acids of the peptide variant (or the nucleic acids of the nucleotide variant) has a degree of identity with respect to the sequence of amino acids (or the nucleic acids) of the peptide (or nucleotide) of interest of at least 70%. In certain embodiments, such sequence identity is at least 80%, at least 85%, at least 90%, at least 95%, or at least 99%.

The term "identity" with respect to a peptide or nucleotide sequence is defined as the percentage of amino acid or nucleic acid residues in a variant sequence that are identical with the amino acid or nucleic acid residues in the peptide or nucleotide of interest, after aligning the sequences and introducing gaps, if necessary, to achieve the maximum percent sequence identity, and not considering any conservative substitutions as part of the sequence identity. Alignment for purposes of determining percent sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

In certain embodiments, the reagent is a variant of the C-terminal segment of moesin that has at least 70% amino acid sequence identity with the amino acid sequence of SEQ ID NO: 3. In certain embodiments, the reagent is a variant of the C-terminal segment of moesin that has at least 80%, at least 85%, at least 90%, at least 95%, or at least 99% amino acid sequence identity with the amino acid sequence of SEQ ID NO: 3.

The term "excipient" as used herein refers to a chemically and pharmaceutically inert ingredient that is included to facilitate the preparation of the dosage forms or to adapt the release of the active ingredients. Excipients include, without limitation, binders, disintegrants, fillers (or diluents), glidants, lubricants, flavours, sweeteners and dyes. The excipients are pharmaceutically acceptable in the sense of being compatible with the other ingredients of the formulation and not unduly deleterious to the recipient thereof; and they may also reduce any undesirable side effects of the active agent. See, Wang et al., *J. Parent. Drug Assn.*, 34(6): 452-462 (1980), which is incorporated herein by reference. Exemplary pharmaceutical excipients suitable for use in the compositions according to the invention are listed in Remington: *The Science & Practice of Pharmacy*, 21$^{st}$ ed., Lippincott Williams & Wilkins (2006); in the *Physician's Desk Reference*, 64$^{th}$ ed., Thomson PDR (2010); and in *Handbook of Pharmaceutical Excipients*, 6$^{th}$ ed., Eds. Raymond C. Rowe et al., Pharmaceutical Press (2009), which are incorporated herein by reference.

An "effective amount" refers to an amount effective, at dosages and for periods of time necessary, to achieve the desired therapeutic or prophylactic result. An effective amount of a reagent of the present application may vary according to factors such as the disease state, age, sex, and weight of the subject, and the ability of the reagent to elicit a desired response in the subject. An effective amount is also one in which any toxic or detrimental effects of the reagent are outweighed by the therapeutically beneficial effects. The determination of the effective amount and appropriate dosage or route of administration is well known within the skill of a person skilled in the art.

In another aspect, the present application relates to use of the C-terminal segment of moesin or a variant thereof for the manufacture of a medicament for treating cancer in a subject.

In another aspect, the present application relates to an isolated nucleotide sequence which encodes for amino acid residues 471-577 of human moesin or variants thereof.

The following examples are presented to illustrate the present application. They are not intended to limiting in any manner.

Example 1

Preparation of Monoclonal Antibodies Bing to the C-Terminal Segment of Moesin or N-Terminal Segment of Moesin Monoclonal antibody against the C-terminal segment of moesin can be prepared by using the conventional hybridoma method. To generate the C-terminal segment of moesin having the sequence of SEQ ID NO: 3, PCR is used to amplify cDNA fragments corresponding to the C-terminal segment as described in SEQ ID NO:3 shown in FIG. 3.

PCR-amplified C-terminal segment moesin DNA fragments are cloned into expression vectors selected from pET32a(+) and pET28a(+). The constructed vectors are then used to transform *E. coli* host cell line BL21 (DE3) for culturing and expression. The constructed expression systems for the C-terminal domain are verified with restriction enzyme digestion followed by sequencing to confirm the correct reading frame for expression of the C-terminal segment.

After sufficient culturing, host cells with expressed C-terminal segment are harvested for collection and purification of the C-terminal segment according to standard protein expression and purification protocols. The resulting protein fragments are assayed with SDS-PAGE to confirm their identity and purity.

The expressed C-terminal segment is then used to make the monoclonal antibody against the C-terminal segment of moesin according to the conventional hybridoma method by using BALB/C mice.

The hybridoma method was first described by Kohler and Milstein, Nature, 256:495 (1975), which is incorporated into the present application in its entirety for reference. In a typical hybridom method, mice (e.g. BALB/C mice) are immunized with an antigen (e.g. the expressed C-terminal segment of moesin as described above) and spleen cells from the immunized mice are then fused with myeloma cells. The fused cells are harvested in a medium which selectively allows growth of hybridomas, and viable hybridoma colonies are grown out. After a sufficient time, supernatants are screened by ELISA testing and immunohistochemical assays using the antigen (e.g. C-terminal segment). Positive cells are selected for further sub-cloning. Selected clones are sub-cloned by limited dilution. Sub-cloning is performed until all clones are ELISA-positive. The positive clones are then selected to obtain hybridomas generating monoclonal antibodies against the antigen.

Antibody against N-terminal segment of moesin protein is prepared in a similar method. The N-terminal segment of moesin used for preparing the antibody has an amino acid sequence as the amino acid residues 1-297 of SEQ ID NO:2 described herein and can be prepared using genetic engineering method as described above.

The antibody against full length or segment of moesin protein is also commercially available.

Example 2

Detection of Specific Segment of Meosin Protein in Sera of Cancer Patients

Sera or plasma samples were collected from patients of various cancer and tested for the presence of specific segment of human moesin, including the N-terminal segment (amino acid residues 1-297), and C-terminal segment (amino acid residues 471-577) using a chemilluminescence enzyme immunoassay. In short, samples were diluted with biotin labeled N-terminal or C-terminal moesin segment for competition in binding to plates coated with antibodies specifically binding to the segment. Enzyme (horseradish peroxidase) labeled streptavidin was then added to bind biotin. After washing, luminescent signals were developed to measure the enzyme-labeled streptavidin bound to the plates. The luminescent signal was inversely proportional to the concentration of the N-terminal or C-terminal segment in the samples.

Materials and Methods

First, wells of a polystyrene micro well plate were coated with highly purified antibodies against N-terminal segment or C-terminal segment of moesin protein under conditions that would preserve the antibody in its native state. Specifically, each micro well of the ELISA plate (LUMITRAC™ 600 96-well white immunology plate, Greiner 655074) was incubated with about 100 ng antibodies against N-terminal segment or C-terminal segment of moesin at 2° C. to 8° C. for 12-16 hours. The plate was then washed with PBS once before being blocked with blocking solution and vacuum dried for storage and later use.

To measure the presence of N-terminal moesin segment in the samples, sera or plasma samples were collected and prepared from patients that were clinically diagnosed as having metastatic sarcoma or non-metastatic sarcoma. Samples from healthy individuals were also collected as control. Samples were diluted using PBS-T buffer (0.05% (v/v) Tween-20) containing 20 ng/ml biotin-labeled N-terminal moesin segment prepared by EZ-Link™ NHS-PEG4-Biotinylation Kit (Thermo Scientific, Product No. 21455). 100 ul of diluted samples were then added to separate wells, allowing biotin-labeled N-terminal moesin segment or any N-terminal moesin segment present in the sample to bind to the immobilized antibody in each well. Unbound N-terminal moesin segment (biotin-labeled or not labeled) was washed away using PBS-T buffer. Streptavidin-HRP (Invitrogen Life Technologies, SA100-01) was then added to each well to bind to the biotin-labeled N-terminal moesin segment attached to the micro wells. After any unbound Streptavidin HRP was washed away, chemiluminescent substrate (Super-Signal ELISA Femto Maximum Sensitivity Substrate, Pierce 37074) was added and the luminescent signal was detected and measured by a luminometer (Thermo Scientific Luminoskan Ascent).

The presence of C-terminal moesin segment was measured using similar method as above.

We also used sandwich ELISA method to determine the presence of full-length moesin protein in the samples. Briefly, plates coated with antibodies against N-terminal moesin segment were prepared as described above. The samples were then added into the plates without being mixed with biotin-labeled N-terminal moesin segment. After unbound proteins were washed, antibodies against C-terminal moesin protein were added to each micro well to detect the presence of full-length moesin protein.

For statistic analysis, student's t-test (two-tail) was employed to assess the difference of N-terminal or C-terminal moesin segment concentration among different groups. The difference was statistically significant when $p<0.05$.

Results

As shown in FIG. 4 and Table 1, samples from cancer patients contained significantly higher concentration of C-terminal moesin segment than healthy individual ($p<0.01$). In comparison, the concentration of N-terminal moesin segment in cancer patient was not statistically significantly higher than healthy individual ($p=0.17$). Full-length meosin protein was not detected in the samples.

As shown in Table 2, C-terminal moesin segment was detected in 70.8% samples from cancer patients but only in 12.5% samples from healthy individuals. In contrast, N-terminal moesin segment was detected in 87.5% samples from cancer patients and in 75% samples from healthy individuals.

Therefore, the presence of C-terminal moesin segment can be used as a biomarker for cancer.

TABLE 1

Concentrations of N-terminal or C-terminal moesin segment in samples.

| Group | Number of patients | Mean Concentration (Standard Deviation) | |
|---|---|---|---|
| | | C-terminal (ng/ml) | N-terminal (ug/ml) |
| Cancer* | 24 | 4.4 (2.2) | 52.5 (165.3) |
| Control | 20 | 0.9 (1.6) | 1.2 (1.4) |

TABLE 2

The presence of N-terminal or C-terminal moesin segment in samples.

| Group | Number of patients | C-terminal | | | N-terminal | | |
|---|---|---|---|---|---|---|---|
| | | + | − | Positive rate (%) | + | − | Positive rate (%) |
| Cancer* | 24 | 17 | 7 | 70.8% | 21 | 3 | 87.5% |
| Control | 20 | 2 | 14 | 12.5% | 12 | 4 | 75.0% |

*Cancer group includes patients of osteosarcoma, Ewing's sarcoma, chondrosarcoma, giant cell tumor, liposarcoma, Non-hodgkin's lymphoma, pancreatic cancer, glioblastoma, breast cancer, ovarian cancer, multiple myeloma, stomach cancer and prostate cancer.

While the invention has been particularly shown and described with reference to specific embodiments (some of which are preferred embodiments), it should be understood by those having skill in the art that various changes in form and detail may be made therein without departing from the spirit and scope of the present application as disclosed herein.

What is claimed is:

1. A method for diagnosing a human subject suspected of having a cancer, the method comprising:
   obtaining a biological sample of the human subject, wherein the biological sample is serum or plasma;
   detecting a level of a C-terminal segment of moesin in the biological sample via an immunoassay, wherein the C-terminal segment of moesin consists of amino acid residues 471-577 of human moesin, and wherein the human moesin has an amino acid sequence of SEQ ID NO: 2;
   comparing the level of the C-terminal segment of moesin detected in the biological sample to a reference level of the C-terminal segment of moesin detected from a reference sample; and
   administering to the human subject a treatment for the cancer when the level of the C-terminal segment of moesin detected in the biological sample is higher than the reference level.

2. The method of claim 1, wherein the level of C-terminal segment of moesin detected in the biological sample is at least 2 times the reference level of the C-terminal segment of moesin.

3. The method of claim 1, wherein the level of C-terminal segment of moesin detected in the biological sample is at least 5 times the reference level of the C-terminal segment of moesin.

4. The method of claim 1, wherein the reference sample is from a non-tumoral subject.

5. The method of claim 1, wherein the cancer is selected from the group consisting of adrenocortical carcinoma, astrocytoma, basal-cell carcinoma, bile duct cancer, bladder cancer, osteosarcoma, brainstem glioma, breast cancer, cervical cancer, colon cancer, cutaneous, Ewing's sarcoma, retinoblastoma, gastric cancer, glioma, head and neck cancer, heart cancer, liver cancer, Hodgkin lymphoma, intraocular melanoma, islet cell carcinoma, kidney cancer, leukemia, lung cancer, melanoma, neuroblastoma, non-Hodgkin lymphoma, ovarian cancer, pancreatic cancer, prostate cancer, and retinoblastoma.

6. The method of claim 5, wherein the cancer is selected from the group consisting of osteosarcoma, Ewing's sarcoma, chondrosarcoma, giant cell tumor, liposarcoma, Non-hodgkin's lymphoma, pancreatic cancer, glioblastoma, breast cancer, ovarian cancer, multiple myeloma, stomach cancer and prostate cancer.

7. The method of claim 1, wherein the treatment is a therapeutic agent or a surgical intervention.

8. The method of claim 7, wherein the therapeutic agent specifically modulates the function of the C-terminal segment of moesin.

9. The method of claim 7, wherein the therapeutic agent specifically binds to the C-terminal segment of moesin.

10. A method for treating a human subject having cancer, the method comprising:
   administering to the human subject a treatment for the cancer,
   wherein a biological sample obtained from the human subject is detected via an immunoassay to have a level of a C-terminal segment of moesin higher than a reference level of the C-terminal segment of moesin detected from a reference sample,
   wherein the C-terminal segment of moesin consists of amino acid residues 471-577 of human moesin,
   wherein the human moesin has an amino acid sequence of SEQ ID NO: 2, and
   wherein the biological sample is serum or plasma.

11. The method of claim 10, wherein the level of C-terminal segment of moesin detected in the biological sample is at least 2 times the reference level of the C-terminal segment of moesin.

12. The method of claim 10, wherein the level of C-terminal segment of moesin detected in the biological sample is at least 5 times the reference level of the C-terminal segment of moesin.

13. The method of claim 10, wherein the reference sample is from a non-tumoral subject.

14. The method of claim 10, wherein the cancer is selected from the group consisting of adrenocortical carcinoma, astrocytoma, basal- cell carcinoma, bile duct cancer, bladder cancer, osteosarcoma, brainstem glioma, breast cancer, cervical cancer, colon cancer, cutaneous, Ewing's sarcoma, retinoblastoma, gastric cancer, glioma, head and neck cancer, heart cancer, liver cancer, Hodgkin lymphoma, intraocular melanoma, islet cell carcinoma, kidney cancer, leukemia, lung cancer, melanoma, neuroblastoma, non-Hodgkin lymphoma, ovarian cancer, pancreatic cancer, prostate cancer, and retinoblastoma.

15. The method of claim 14, wherein the cancer is selected from the group consisting of osteosarcoma, Ewing's sarcoma, chondrosarcoma, giant cell tumor, liposarcoma, Non-hodgkin's lymphoma, pancreatic cancer, glioblastoma, breast cancer, ovarian cancer, multiple myeloma, stomach cancer and prostate cancer.

16. The method of claim 10, wherein the treatment is a therapeutic agent or a surgical intervention.

17. The method of claim 16, wherein the therapeutic agent specifically modulates the function of the C-terminal segment of moesin.

18. The method of claim 16, wherein the therapeutic agent specifically binds to the C-terminal segment of moesin.

* * * * *